US010874526B1

(12) United States Patent
McClellan

(10) Patent No.: US 10,874,526 B1
(45) Date of Patent: Dec. 29, 2020

(54) PERIPHERAL VERTEBRAL BODY SPACER IMPLANT AND INSERTION TOOL

(71) Applicant: John W. McClellan, Omaha, NE (US)

(72) Inventor: John W. McClellan, Omaha, NE (US)

( * ) Notice: Subject to any disclaimer, the term of this patent is extended or adjusted under 35 U.S.C. 154(b) by 39 days.

(21) Appl. No.: 16/021,139

(22) Filed: Jun. 28, 2018

Related U.S. Application Data

(60) Division of application No. 15/441,827, filed on Feb. 24, 2017, now Pat. No. 10,034,776, which is a continuation of application No. 13/037,488, filed on Mar. 1, 2011, now Pat. No. 9,579,214.

(51) Int. Cl.
*A61F 2/46* (2006.01)

(52) U.S. Cl.
CPC ..... *A61F 2/4611* (2013.01); *A61F 2002/4627* (2013.01); *A61F 2002/4628* (2013.01); *A61F 2002/4629* (2013.01)

(58) Field of Classification Search
CPC ........ A61F 2/46; A61F 2/4603; A61F 2/4611; A61F 2002/4622; A61F 2002/4623; A61F 2002/4624; A61F 2002/4625; A61F 2002/4627; A61F 2002/4628; A61F 2002/4629; A61F 2002/4687
USPC .................................................. 606/99, 100
See application file for complete search history.

(56) References Cited

U.S. PATENT DOCUMENTS

| | | | |
|---|---|---|---|
| 5,489,307 A * | 2/1996 | Kuslich | A61B 17/1757 128/898 |
| 5,989,259 A * | 11/1999 | Penenberg | A61F 2/4607 606/102 |
| 6,206,923 B1 | 3/2001 | Boyd et al. | |
| 6,241,729 B1 * | 6/2001 | Estes | A61B 17/025 606/86 R |
| 6,558,424 B2 | 5/2003 | Thalgott | |
| 6,575,899 B1 * | 6/2003 | Foley | A61B 1/00105 600/102 |
| 6,638,310 B2 | 10/2003 | Lin et al. | |
| 7,056,341 B2 | 6/2006 | Crozet | |
| 7,507,243 B2 * | 3/2009 | Lambrecht | A61B 5/1076 606/92 |
| 7,875,034 B2 * | 1/2011 | Josse | A61B 17/025 606/90 |
| 8,147,556 B2 | 4/2012 | Louis et al. | |
| 8,231,678 B2 * | 7/2012 | Lambrecht | A61F 2/4611 623/17.11 |
| 9,387,087 B2 * | 7/2016 | Tyber | A61F 2/4455 |
| 9,579,214 B1 * | 2/2017 | McClellan | A61F 2/4455 |
| 9,724,135 B2 * | 8/2017 | Koch | A61B 17/3421 |
| 10,034,776 B1 * | 7/2018 | McClellan | A61F 2/4465 |
| 2002/0045945 A1 * | 4/2002 | Liu | A61F 2/446 623/17.16 |
| 2002/0077641 A1 * | 6/2002 | Michelson | A61B 17/025 606/167 |
| 2003/0069586 A1 * | 4/2003 | Errico | A61F 2/442 606/99 |

(Continued)

*Primary Examiner* — Eric S Gibson

(74) *Attorney, Agent, or Firm* — Suiter Swantz pc llo

(57) ABSTRACT

An intervertebral stabilization implant and an intervertebral stabilizer insertion tool are disclosed. The insertion tool inserts the implant between the posterior peripheral regions of two vertebral bodies, and has elements allowing the insertion tool to position the implant and remove the implant if necessary. The insertion tool engages interior surfaces of an interlockable implant cavity to reduce the amount of space necessary to position the implant.

2 Claims, 11 Drawing Sheets

(56) References Cited

U.S. PATENT DOCUMENTS

| | | | |
|---|---|---|---|
| 2003/0083747 A1* | 5/2003 | Winterbottom | A61F 2/28 623/17.11 |
| 2003/0199874 A1* | 10/2003 | Michelson | A61B 17/025 606/86 A |
| 2004/0260300 A1* | 12/2004 | Gorensek | A61F 2/4611 606/86 R |
| 2004/0260305 A1* | 12/2004 | Gorensek | A61F 2/4611 606/99 |
| 2005/0021042 A1* | 1/2005 | Marnay | A61F 2/4425 606/99 |
| 2005/0107879 A1 | 5/2005 | Christensen et al. | |
| 2005/0113842 A1* | 5/2005 | Bertagnoli | A61B 17/025 606/90 |
| 2005/0119753 A1 | 6/2005 | McGahan et al. | |
| 2005/0283239 A1 | 12/2005 | Crozet | |
| 2006/0085011 A1* | 4/2006 | Filippi | A61B 17/1757 606/99 |
| 2006/0200166 A1 | 9/2006 | Hanson et al. | |
| 2006/0200246 A1* | 9/2006 | Lambrecht | A61F 2/442 623/17.16 |
| 2006/0265076 A1* | 11/2006 | Carter | A61F 2/441 623/17.16 |
| 2006/0276800 A1* | 12/2006 | Lee | A61B 17/1671 606/90 |
| 2006/0293748 A1* | 12/2006 | Alexander | A61F 2/447 623/17.11 |
| 2007/0010886 A1 | 1/2007 | Banick et al. | |
| 2007/0016217 A1* | 1/2007 | Dinville | A61B 17/1671 606/99 |
| 2007/0093897 A1 | 4/2007 | Gerbec et al. | |
| 2007/0191857 A1* | 8/2007 | Allard | A61B 17/1757 606/90 |
| 2008/0082169 A1* | 4/2008 | Gittings | A61B 17/025 623/17.16 |
| 2008/0103602 A1 | 5/2008 | Berry et al. | |
| 2008/0161927 A1 | 7/2008 | Savage et al. | |
| 2008/0269764 A1* | 10/2008 | Blain | A61B 17/025 606/99 |
| 2008/0275455 A1* | 11/2008 | Berry | A61F 2/4611 606/99 |
| 2008/0306596 A1 | 12/2008 | Jones et al. | |
| 2009/0216330 A1* | 8/2009 | Geisert | A61B 17/1671 623/17.16 |
| 2010/0087830 A1* | 4/2010 | Dace | A61B 17/1671 606/99 |
| 2010/0298941 A1* | 11/2010 | Hes | A61F 2/4425 623/17.16 |
| 2011/0178599 A1 | 7/2011 | Brett | |
| 2011/0230970 A1* | 9/2011 | Lynn | A61F 2/442 623/17.16 |
| 2012/0116466 A1* | 5/2012 | Dinville | A61F 2/447 606/86 A |
| 2012/0197404 A1* | 8/2012 | Brun | A61F 2/447 623/17.16 |
| 2012/0271312 A1* | 10/2012 | Jansen | A61B 17/1604 606/80 |
| 2012/0310348 A1* | 12/2012 | Pafford | A61L 27/54 623/17.16 |
| 2013/0006365 A1* | 1/2013 | Pepper | A61F 2/447 623/17.16 |
| 2013/0226244 A1* | 8/2013 | Davenport | A61F 2/4465 606/279 |
| 2013/0226253 A1* | 8/2013 | Davenport | A61F 2/4465 606/86 A |
| 2014/0114415 A1* | 4/2014 | Tyber | A61F 2/4455 623/17.16 |
| 2015/0032220 A1* | 1/2015 | Tyber | A61B 17/8095 623/23.5 |
| 2016/0058563 A1* | 3/2016 | Zappacosta | A61B 17/0642 623/17.16 |
| 2016/0120556 A1* | 5/2016 | Bertagnoli | A61B 17/1671 606/79 |
| 2017/0100260 A1* | 4/2017 | Duffield | A61F 2/4611 |
| 2017/0296207 A1* | 10/2017 | Bertagnoli | A61B 17/1671 |

* cited by examiner

PERIPHERAL VERTEBRAL BODY SPACER IMPLANT AND INSERTION TOOL

PRIORITY

The present application claims the benefit under 35 U.S.C. § 120 of U.S. patent application Ser. No. 15/441,827 (filed Feb. 24, 2017), which claimed the benefit of U.S. patent application Ser. No. 13/037,488 (filed Mar. 1, 2011), now U.S. Pat. No. 9,579,214, which are incorporated herein by reference.

FIELD OF THE INVENTION

The present invention relates to implantable spinal prostheses, and specifically to implantable intervertebral spacers for stabilizing vertebrae in a vertebral column.

BACKGROUND OF THE INVENTION

Vertebral fusion is a common surgical procedure to immobilize two or more vertebrae. In surgical fusion, implants immobilize the vertebrae relative to each other while osteoblastic, or bone-growth inducing material stimulates bone growth between the vertebrae.

Surgeons perform vertebral fusion as a last resort to treat pain or neurological deficits caused by vertebral column abnormalities. Abnormalities indicating fusion include degenerative disc disease, disc herniation, discognetic pain, spinal tumors, vertebral fractures, scoliosis, kyphosis, spondylolisthesis, spondylosis, and Posterior Rami Syndrome. Posterolateral fusion immobilizes the vertebrae with metal implants connected to screws and wires through the pedicles of each vertebrae and bone grafts between the transverse processes. Interbody fusion immobilizes the vertebrae by replacing the cartilaginous disc between the vertebrae with an implant and bone graft. Surgeons generally perform interbody fusion between vertebrae in either the cervical spine or the lumbar spine.

Orthopedic surgeons perform anterior cervical interbody fusion through a small incision in the patient's neck, approaching the cervical spine from the anterior side. Retractors protect vascular and neurological structures on each side of the cervical spine while the surgeon removes the unhealthy cartilage by ablation or some other equivalent process.

Once the surgeon has removed the unhealthy cartilage, he inserts an implant into the disc space between the two cervical vertebrae. Current implants have two shortcomings; the surgeon cannot safely place an implant where it would be most effective; and the surgeon cannot ensure that bone-growth inducing material has made contact with both vertebrae, which is necessary to ensure successful fusion. Both shortcomings are common to implants used in lumbar interbody fusion as well.

Surgeons must generally insert existing implants by gripping the implant along its circumference with forceps and sliding the implant into the disc space. Alternatively, the surgeon may insert the implant by gripping the implant along the top and bottom surfaces and sliding the implant into the disc space. Either method usually requires light hammering with a mallet to fully insert the implant.

These insertion methods have significant drawbacks: gripping the implant along its circumference necessarily requires the implant to have a smaller circumference than the disc space the implant is intended to fill; otherwise the surgeon could not remove the forceps he used to insert the implant. For the same reason, gripping the implant by the top and bottom necessarily requires the surgeon to remove the holder before fully seating the implant. In either case, the surgeon performing the operation will usually use a small mallet and impact tool to tap the implant further into the disc space. While tapping is an effective and controllable means of inserting the implant, tapping also imparts significant loads on the implant that may cause cracking. Furthermore, a surgeon generally cannot pull an implant back if the surgeon taps the implant too far into the disc space, and tapping an implant too far into the disc space poses a danger to the patient's spinal cord; therefore, surgeons usually do not place existing implants in the region of the disc space between the dense cortical bone at the posterior peripheral regions of the vertebrae, even though such placement would provide ideal support.

Instead, surgeons generally place existing implants in the center of the disc space. The center of a vertebral body is softer than the periphery of the vertebral body because the center is composed primarily of cancellous bone which is porous; therefore, implants placed in the center of the vertebral body often subside.

Existing implants include one or more bone-growth inducing material containers defined by the circumference of the implant. Bone-growth inducing material stimulates new bone formation in the disc space where the surgeon has removed the unhealthy cartilage, thereby fusing the two adjacent vertebrae. Because existing implants completely circumscribe the bone-growth inducing material containers, a surgeon must pack bone-growth inducing material into those containers before the surgeon inserts the implant into the patient's vacant disc space. During insertion, bone-growth inducing material frequently settles or subsides, or otherwise fails to make contact with each of the vertebra defining the empty disc space. If the bone-growth inducing material does not make contact with both vertebrae, the vertebrae may never actually fuse and the operation will be a failure. Because existing implants completely circumscribes the bone-growth inducing material containers, the surgeon has no way of knowing if the bone-growth inducing material has made contact with each vertebra; nor does the surgeon have an effective means of correcting the situation if not.

Fusion failure is common. Fusion failure typically occurs when the implant subsides into the cancellous bone of the vertebrae, or when the bone-growth inducing material does not properly interface with the vertebrae. Consequently, it would be advantageous if an apparatus existed that is suitable for stabilizing vertebrae, which can be positioned precisely along the posterior peripheral cortical bone regions of two vertebrae, and which a surgeon can pack with bone-growth inducing material after the apparatus is in place.

SUMMARY OF THE INVENTION

Accordingly, the present invention is directed to an intervertebral stabilization apparatus which can be positioned precisely along the posterior peripheral cortical bone regions of two vertebrae, and which a surgeon can pack with bone-growth inducing material after the apparatus is in place. The present invention is also directed to an intervertebral stabilizer insert tool for such an implant.

An intervertebral stabilization implant according to the present invention may have an intervertebral spacer to transfer a load between respective peripheral regions of two adjacent vertebral bodies, where the bone comprising the vertebrae is most dense. Specifically, a surgeon may insert the intervertebral spacer between posterior peripheral regions of the two vertebrae. The vertebral stabilization implant may have an interlockable cavity defined by the intervertebral spacer, shaped to provide a contact surface for positioning the intervertebral stabilization implant. The interlockable cavity may be open on three sides so that a surgeon may pack bone-growth inducing material into the interlockable cavity after inserting the intervertebral stabilization implant, and the bone-growth inducing material will contact both vertebrae.

An intervertebral stabilizer insertion tool according to the present invention may have an interlockable positioning head to interlock with an interlockable cavity of an intervertebral stabilization implant, and thereby control the positioning of the intervertebral stabilization implant. The intervertebral stabilizer insertion tool may also have an adjustable depth control stop allowing a surgeon to precisely place the implant at the back of the disc space, based on the surgeon's measurements, while preventing the surgeon from inserting the intervertebral stabilization implant beyond the posterior cortical bone regions of the adjacent vertebral bodies.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous objects and advantages of the present invention may be better understood by those skilled in the art by reference to the accompanying figures in which.

DETAILED DESCRIPTION OF THE INVENTION

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

Vertebral fusion is a common surgical treatment for damaged or otherwise unhealthy intervertebral discs in the cervical or lumbar regions of a patient's vertebral column where a surgeon replaces the unhealthy disc with an implant. Current implants have significant drawbacks; the present invention is directed toward an intervertebral stabilization implant and an intervertebral stabilizer insertion tool that correct those drawbacks.

Figure 1:
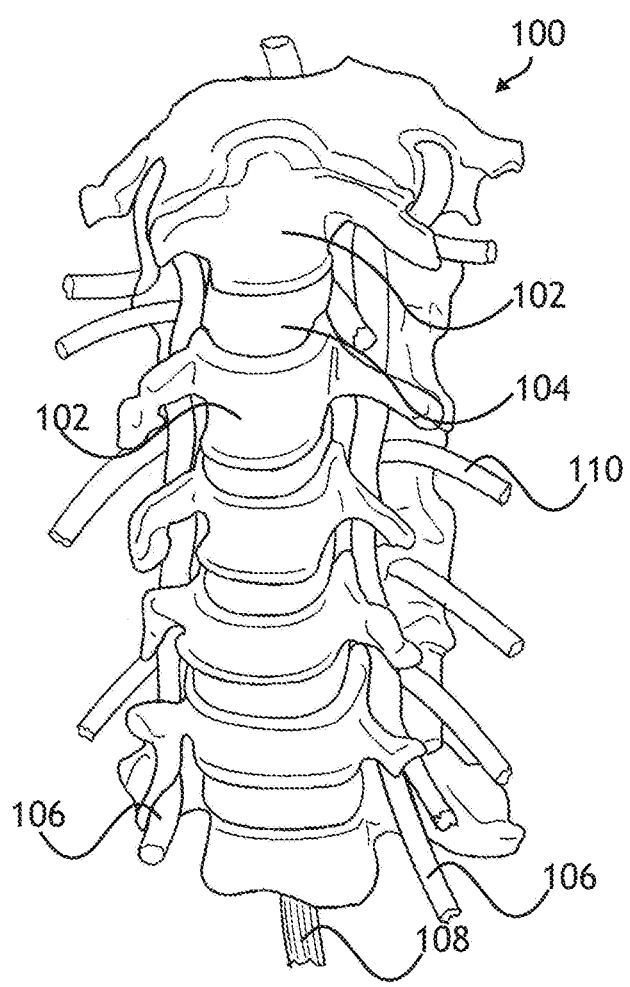
FIG. 1 shows a perspective view of a portion of a vertebral column.

Referring to FIG. 1, the present invention relates to an implantable apparatus for stabilizing a vertebral column when a surgeon determines that a damaged or deteriorating cartilaginous intervertebral disc must be removed. FIG. 1 shows a portion of a vertebral column 100. The portion of the vertebral column 100 consists of multiple vertebrae 102, cartilaginous intervertebral discs 104 disposed between adjacent vertebrae 102, blood vessels 106 running through openings or foramen in the vertebrae 102, and nerves 110 branching off from a spinal cord 108 to enervate various parts of the patient's body. When a patient suffers damage or deterioration to a cartilaginous intervertebral disc 104, the unhealthy disc 104 may no longer support the weight of the patient's body. The vertebrae 102 above an unhealthy disc 104 may shift position and put pressure on nerves 110 originating from the spinal cord 108 near the vertebrae 102, causing the patient significant pain. Surgeons routinely treat pain caused by an unhealthy disc 104 by surgical fusion. During surgical fusion, a surgeon removes the unhealthy disc 104, and immobilizes the vertebrae 102 immediately above and below the unhealthy disc 104 relative to each other.

As currently practiced, the surgeon immobilizes the vertebrae 102 with an implant made of either a surgical grade plastic such as polyether ether ketone (PEEK), bone harvested from the patient, or metal suitable for surgical implantation such as titanium. The implant generally has a cavity where the surgeon may pack a bone-growth inducing material to encourage the vertebrae 102 to grow together or "fuse." If the procedure is successful, new bone replaces the unhealthy disc 104, thereby immobilizing the adjacent vertebrae 102 relative to each other, and preventing any unusual pressure on the nerves 110 originating from the spinal cord 108 in the region between the two vertebrae 102. In situations where the patient has multiple unhealthy discs 104, a surgeon may fuse multiple sets of vertebrae 102.

Figure 2:
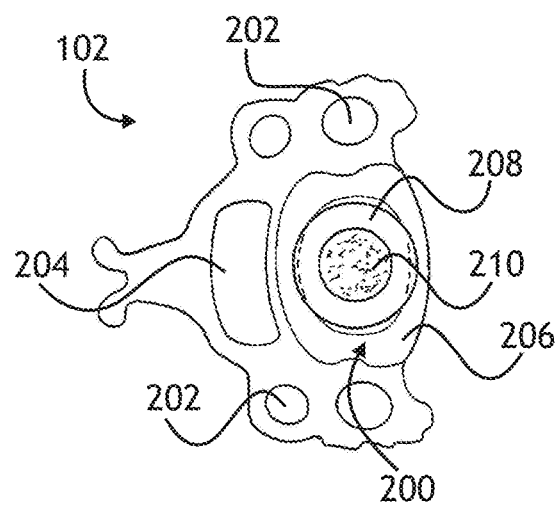
FIG. 2 shows a top view of one embodiment of a prior art vertebral spacer.
Figure 3:
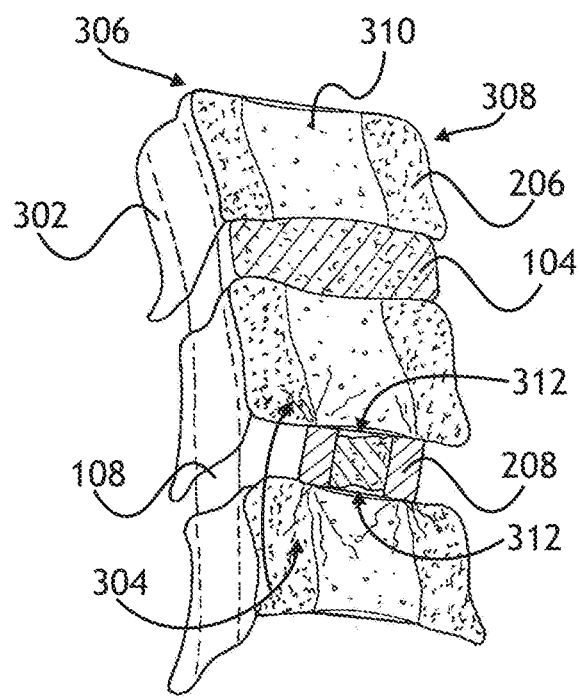
FIG. 3 shows a side, sectional view of one embodiment of a prior art vertebral spacer in a vertebral column.
Figure 4:
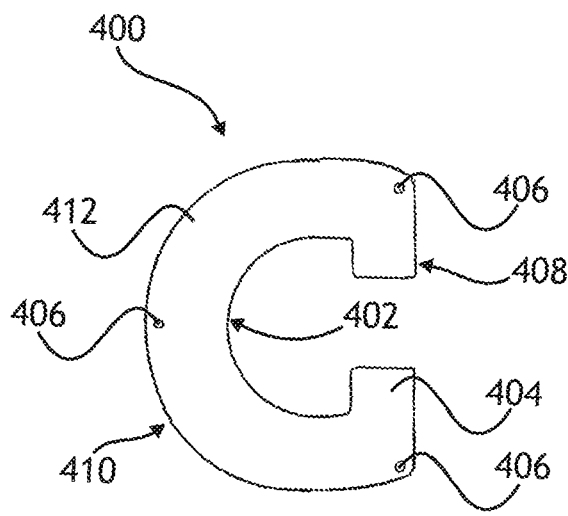
FIG. 4 shows a top view of one embodiment of an intervertebral stabilization implant according to the present invention.
Figure 5:
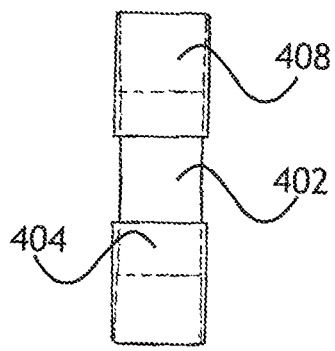
FIG. 5 shows a front view of the embodiment shown in FIG. 4.
Figure 6:
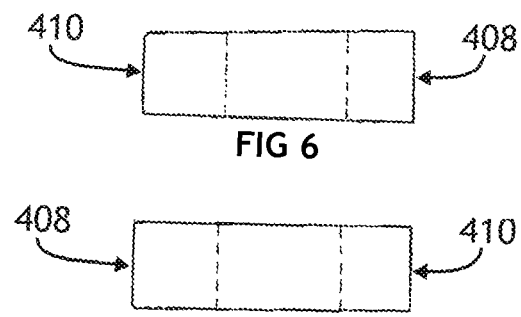
FIG. 6 shows a side view of the embodiment shown in FIG. 4.
Figure 7:
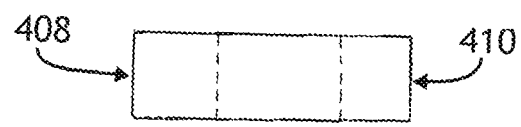
FIG. 7 shows a side view of the embodiment shown in FIG. 4.

Unfortunately, existing vertebral implants have serious drawbacks. Referring to FIG. 2 and FIG. 3, a vertebral body 200 consists of cancellous bone 310 surrounded by a ring of cortical bone know as the cortical rim 206 or apophyseal ring. The cortical rim 206 forms a slight ridge around the periphery of the vertebral body 200.

Cortical bone is denser than cancellous bone 310, and is therefore better suited to support a patient's weight. However, surgeons generally position prior art implants 208 almost entirely between the cancellous bone 310 regions of the vertebral bodies 200. Surgeons position implants 208 in the center of the vertebral body 200, and consequently between regions of cancellous bone 310, because space it is difficult and hazardous to position the implant 208 between the denser and more suitable cortical rims 206 of the two vertebrae 102 being fused. For example, in the cervical spine, blood vessels 106 pass through the vertebrae 102 in the foramen transversium 202; improper positioning of the implant 208 could restrict blood flow through those blood vessels 106. Likewise, the patient's spinal cord 108 passes through the vertebrae 102 in the vertebral or spinal canal 204; improper positioning of the implant 208 could damage or put pressure on the spinal cord 108. Furthermore, techniques for inserting the implant 208 do not allow the surgeon to easily reposition the implant 208, or to precisely set the depth of the implant 208, as defined by the distance from the implant 208 to the anterior region 308 of the vertebral body 200. Without the ability to precisely control the positioning and depth of the implant 208, surgeons must err on the side of caution by placing the implant 208 where it is least likely to damage blood vessels 106 or spinal cord 108.

Prior art implants 208 are also generally too small to fill the space where an unhealthy disc 104 has been removed. Surgeons insert an implant 208 by gripping the sides of the implant 208 with forceps and sliding the implant 208 at least partially into the space between two vertebral bodies 200 previously occupied by the unhealthy disc 104. The implant 208 must necessarily be small enough for the surgeon to subsequently remove the forceps without damaging blood vessels 106 or nerves 110. An implant 208 large enough to interpose between the cortical rims 206 of two adjacent vertebrae 102 would be too large to safely insert with forceps. For these reasons, surgeons generally position implants 208 between the centers of adjacent vertebral bodies 200, with cancellous bone 310 above and below of the implant 208. This positioning places the entire load originating above the implant 208 on the less dense cancellous bone 310. Cancellous bone 310 deforms and subsides 304 when under such loads.

Furthermore, prior art implants 208 fit tightly between adjacent vertebrae 102 and usually require light hammering with a mallet to drive the implant 208 from the insertion point near the anterior region 308 of the vertebral body 200 toward the posterior region 306 of the vertebral body 200. Hammering can cause fractures in the implant 208, especially where the implant 208 is made of bone harvested from the patient. Fractures weaken the structural integrity of the implant 208.

Finally, a surgeon must pack bone-growth inducing material 210 into prior art implants 208 before insertion because the bone-growth inducing material 210 container is inaccessible once the surgeon has positioned the implant 208. Bone-growth inducing material 210 frequently shifts and compacts within the implant 208, or falls out altogether due to shifting and hammering during insertion. Gaps 312 may form between the bone-growth inducing material 210 and one or both vertebrae 102, in which case new bone growth may never occur and the vertebrae 102 will not fuse.

A surgeon's inability to safely and reliably position the prior art implant 208 in a dense region of cortical bone, or to pack bone growth-inducing material 210 into the implant 208 after the implant 208 is in place are significant drawbacks to present technology.

Referring to FIG. 4, FIG. 5, FIG. 6 and FIG. 7, an intervertebral stabilization implant 400 according to one embodiment of the present invention may have an intervertebral spacer 412 to transfer a load from the cortical rim 206 of one vertebral body 200 to the cortical rim 206 of another vertebral body 200 in a vertebral column 100 where a surgeon has removed a damaged or deteriorated cartilaginous intervertebral disc 104 from between two vertebrae 102. The intervertebral spacer 412 may substantially correspond to the shape of the cortical rim 106 of whichever two vertebrae 102 the intervertebral stabilization implant 400 will stabilize. The precise shape and size of the cortical rim 106 of a vertebra 102 may vary depending on the location of the vertebrae 102 in the spinal column 100. The intervertebral spacer 412 may be thicker at the anterior 408 than at the posterior 410 to more closely conform to the shape of the disc space where the surgeon removed the cartilaginous intervertebral disc 104, which is generally wider toward the anterior region 308 of the vertebral body 200 than the posterior region 306 of the vertebral body 200.

The intervertebral stabilization implant 400 may have an interlockable cavity 402 defined by the intervertebral spacer 412 to provide a surface for positioning the intervertebral stabilization implant 400 with an intervertebral stabilizer insertion tool. The interlockable cavity 402 provides a means for a surgeon to manipulate the intervertebral stabilization implant 400 without gripping the implant 400 along the outside periphery. An intervertebral stabilizer insertion tool would engage the interlockable cavity 402 such that, during insertion into a vertebral column 100, a linear force applied to the insertion tool would be transferred to the intervertebral stabilization implant 400 to drive the implant 400 from the anterior region 308 of the vertebral body 200 toward the posterior region 306 of the vertebral body 200.

The interlockable cavity 402 may provide a broad contact surface to transfer a load from an insertion tool to the implant 400. Whereas prior art implants 108 often fractured during hammering, an intervertebral stabilization implant 400 with an interlockable cavity 402 according to the present invention may be less prone to fracture during hammering because the broader contact surface may spread the load.

The intervertebral stabilization implant 400 may have one or more position control arms 404 disposed on the intervertebral spacer 412. Position control arms 404 further define the contact surface of the interlockable cavity to transfer a force to the implant 400 to rotate the implant 400 about an axis substantially parallel to an axis defined by a vertebral column 100 into which a surgeon is inserting the implant 400. The position control arms 404 may protrude from opposing ends of the intervertebral spacer 412 along the anterior surface 408 of the implant 400 to engage one or more retractable positioning arms of an insertion tool. The position control arms 404 may also provide a surface to transfer a linear force to the implant 400 to withdraw the implant 400, or move the implant from the posterior region 306 of the vertebral body 200 toward the anterior region 308 of the vertebral body 200; effectively backing the implant 400 out if a surgeon believes the implant has been inserted too far.

A surgeon inserting an intervertebral stabilization implant 400 with position control arms 404 according to the present invention may be able to turn the implant 400 while wholly or partially within a vertebral column 100, and thereby orient the implant 400 to maximize contact between the intervertebral spacer 412 and the cortical rim 206 of the adjacent vertebral bodies 200. A surgeon may also turn the implant 400 during insertion to orient the insertion tool before lightly hammering a strike surface on the insertion tool. By turning and orienting the insertion tool, a surgeon may precisely control the linear force applied to the implant 400 during insertion, and thereby position the implant 400 to transfer a load in a vertebral column 100 from the cortical rim 206 of one vertebral body 200 to the cortical rim 206 of another vertebral body 200 without significant risk to nearly blood vessels 106 and nerves 110.

An intervertebral stabilization implant 400 according to the present invention may also have one or more radio opaque positioning rods 406 embedded in the implant 400 at one or more pre-determined locations to allow a radiologist to precisely determine the location and orientation of the implant 400 after insertion. An implant 400 according to the present invention may be comprised of a material such as PEEK which is not visible by radiological imaging. Radio opaque positioning rods 406 embedded in the implant 400 may be visible by radiological imaging; by their position and orientation in a radiological image, and their known position and orientation in the implant 400, a radiologist may determine the relative position of the implant 400 within a patient. Radio opaque positioning rods 406 may be comprised of any radio opaque material that is safe for surgical implantation in a vertebral column 100 such as titanium.

Figure 8:
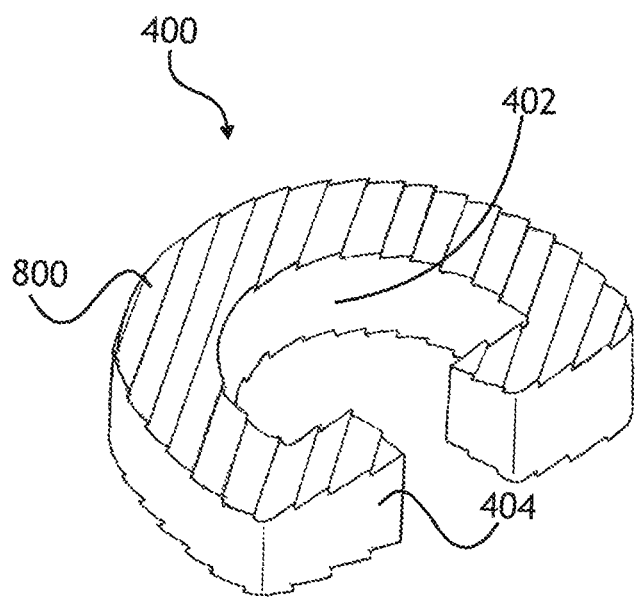
FIG. 8 shows a perspective view of one embodiment of an intervertebral stabilization implant according to the present invention.

Referring to FIG. 8, an intervertebral stabilization implant 400 according to the present invention may also have one or more bone friction enhancing protrusions 800 disposed on one or more surfaces of the intervertebral spacer 412 where the intervertebral spacer 412 contacts the cortical rim 206 of a vertebral body 200. Bone friction enhancing protrusions 800 give a surgeon more complete control over the positioning of an implant 400 because bone friction enhancing protrusions 800 increase the force necessary to move the implant 400, and thereby reduce the likelihood that the implant 400 will accidentally move during insertion. Bone friction enhancing protrusions 800 also reduce the risk of an implant 400 shifting from its final position between the cortical rims 206 of adjacent vertebral bodies 200 after insertion. Bone friction enhancing protrusions 800 may take any form, safe for surgical implantation in a vertebral column 100, likely to induce a higher coefficient of friction against bone as compared to an implant 400 without one or more bone friction enhancing protrusions 800, including structural elements such as serrations disposed on the intervertebral spacer 412.

A surgeon inserting an intervertebral stabilization implant 400 according to the present invention may precisely control the position and orientation of the implant 400 to place the implant between dense regions of cortical bone in a patient's vertebral column. Furthermore, the surgeon may position the implant 400 before packing bone-growth inducing material 210 into the interlockable cavity 402, and thereby ensure that bone-growth inducing material 210 makes contact with both adjacent vertebrae 102.

Figure 9:
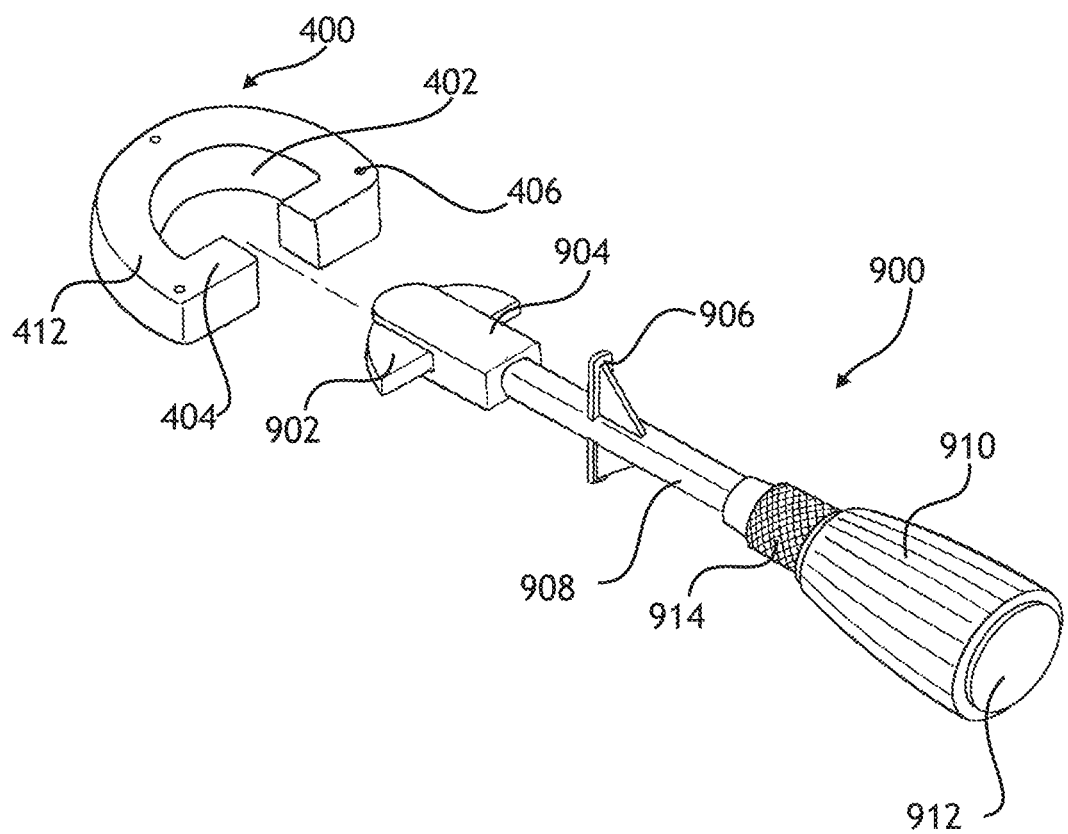
FIG. 9 shows a perspective view of one embodiment of an intervertebral stabilization implant and one embodiment of an intervertebral stabilizer insertion tool according to the present invention.
Figure 10:
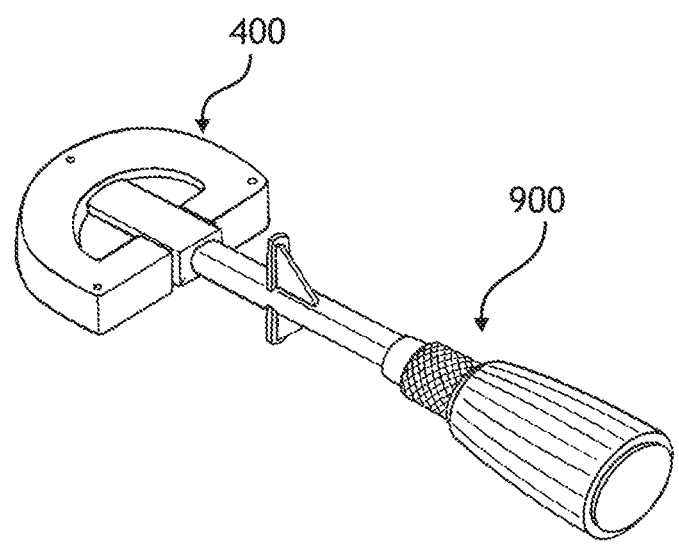
FIG. 10 shows a perspective view of the intervertebral stabilization implant and intervertebral stabilizer insertion tool shown in FIG. 9, combined for inserting the intervertebral stabilization implant into a vertebral column.

A surgeon inserts the intervertebral stabilization implant 400 through an incision in the patient's neck. The surgeon must have a tool for inserting and positioning the implant 400 through such an incision Referring to FIG. 9 and FIG. 10, an embodiment of an intervertebral stabilizer insertion tool 900 according to the present invention may have a handle 910 with a strike surface 912 disposed on the proximal end of the handle 910, and an elongated shaft 908 extending from the distal end of the handle 910. The intervertebral stabilizer insertion tool 900 may also have a retractable positioning arm retracting knob 914 at the distal send of the handle 910 to operate a retractable positioning arm actuator as more fully described below. One or more retractable positioning arms 902 may be functionally connected to an interlockable positioning head 904, with the interlockable positioning head 904 disposed on the distal end of the shaft 908. A surgeon using the intervertebral stabilizer insertion tool may operate the retractable positioning arm retracting knob to retract the retractable positioning arms 902 into the interlockable positioning head 904 as described in further detail below. The retractable positioning arms 902 and interlockable positioning head 904 may engage an interlockable cavity 402 of an intervertebral stabilization implant 400. When the retractable positioning arms 902 and interlockable positioning head 904 engage an interlockable cavity 402 in an intervertebral stabilization implant 400, the interlockable positioning head transfers a linear force applied to the intervertebral stabilizer insertion tool 900 along the axis of the shaft 908 to the implant 400;

for example, when a surgeon strikes the strike surface 912 with a mallet, the surgeon drives an interlocked implant 400 toward the posterior region 306 of a vertebral body 200; or when a surgeon pulls the handle 910 along the axis of the shaft 908 in the opposite direction, the surgeon pulls an interlocked implant 400 toward the anterior region 308 of a vertebral body 200. Likewise, the retractable positioning arms 902 may also transfer to the implant 400 a rotational force applied to the intervertebral stabilizer insertion tool 900 in a plane defined by the retractable positioning arms 902. Such a rotational force may cause one or more retractable positioning arms 902 to push a contact surface of an interlockable cavity 402 defined by an intervertebral spacer 412, and further defined by one or more position control arms 404 disposed on the intervertebral spacer 412. Such a rotational force may also cause the interlockable positioning head 904 to push a contact surface of an interlockable cavity 402 defined by the intervertebral spacer 412, and further defined by one or more position control arms 404 disposed on the intervertebral spacer 412. Contact between position control arms 404 of the implant 400 and retractable positioning arms 902 and the interlockable positioning head 904 of the intervertebral stabilizer insertion tool 900 may impart a rotational force on the implant 400, allowing a surgeon to change the orientation of the implant 400 during insertion.

The intervertebral stabilizer insertion tool 900 may also have one or more depth control posts 906. The depth control posts 906 may be disposed on the elongated shaft 908 and protrude substantially perpendicular to the primary axis of the shaft 908. The depth control posts 906 prevent a surgeon from inserting an intervertebral stabilization implant 400 too far into a vertebral column 100 by making contact with one or more vertebrae 102 when the implant 400 has reached an appropriate depth. Depth control posts 906 may be fixed to a shaft 908 or they may be adjustable as more fully described below.

A surgeon combines an intervertebral stabilization implant 400 with an intervertebral stabilizer insertion tool 900 by interlocking the interlockable positioning head 904 and the insertion tool 900 with the interlockable cavity 402 of the implant 400. The surgeon may then insert the implant 400 into a disc space in a patient's vertebral column 100 through an incision in the patient's neck. The surgeon controls the position and orientation of the implant 400 by manipulating the insertion tool 900.

Figure 11:
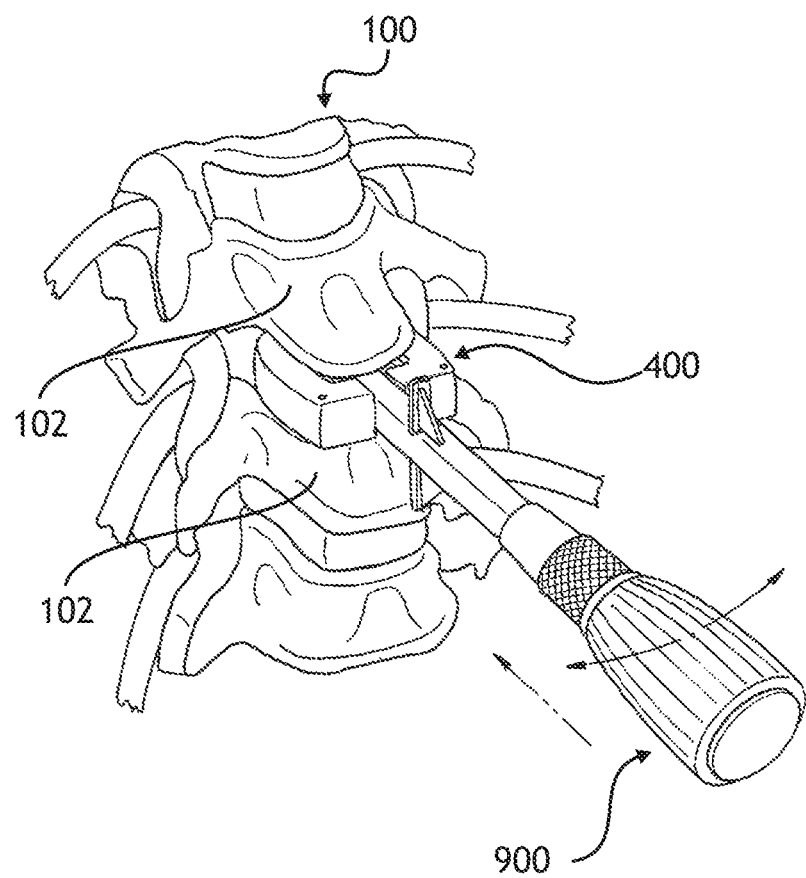
FIG. 11 shows a perspective view of the combined intervertebral stabilization implant and intervertebral stabilizer insertion tool shown in FIG. 10, inserting the intervertebral stabilization implant into a vertebral column.
Figure 12:
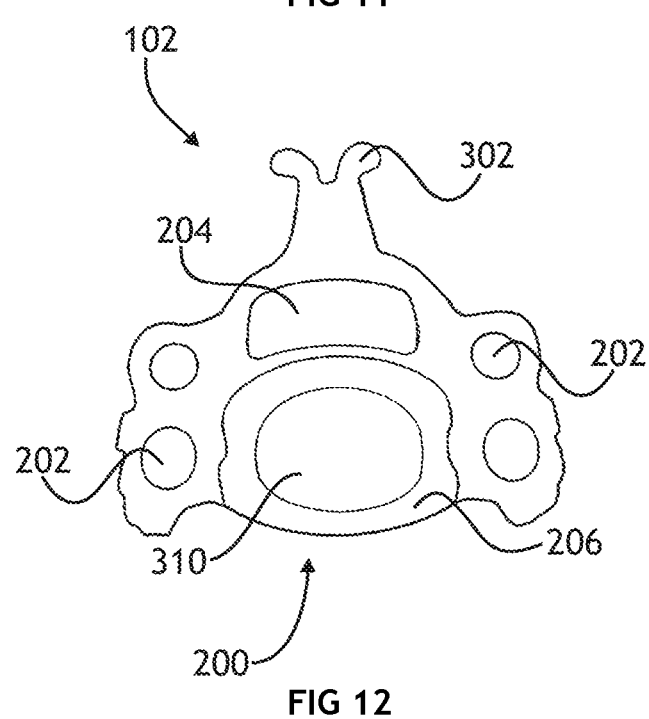
FIG. 12 shows a top view of a vertebrae before an intervertebral stabilization implant has been inserted.

Referring to FIG. 11 and FIG. 12, a surgeon inserting one embodiment of an intervertebral stabilization implant 400 according to the present invention, using an intervertebral stabilizer insertion tool 900 according to the present invention, removes an unhealthy cartilaginous intervertebral disc 104 from between two vertebrae 102 in a vertebral column 100. The surgeon may remove the disc 104 by ablation, or any means known in the art. Once the surgeon has removed the disc 104, the surgeon may combine the intervertebral stabilization implant 400 with the intervertebral stabilizer insertion tool by engaging an interlockable positioning head 904 of the insertion tool 900 with an interlockable cavity 402 of the implant 400. The interlockable positioning head 904 may have retractable positioning arms 902 that also engage the interlockable cavity 402. The shaft 908 of the insertion tool 900 or the interlockable positioning head 904 of the insertion tool 900 may extend from the implant 400 between opposing position control arms 404 disposed on an intervertebral spacer 412 of the implant 400. A surgeon may insert the implant 400 between the vertebral bodies 200 of two adjacent vertebrae 102 so that an intervertebral spacer 412 of the implant 400 interposes between the cortical rims 206 of the adjacent vertebral bodies 200.

A surgeon may achieve optimal vertebral stabilization if the surgeon places the implant 400 such that the intervertebral spacer 412 interposes between the cortical rims 206 of adjacent vertebral bodies 200, toward the posterior regions 306 of the vertebral bodies 200, adjacent to the spinal canal 204.

Figure 13:
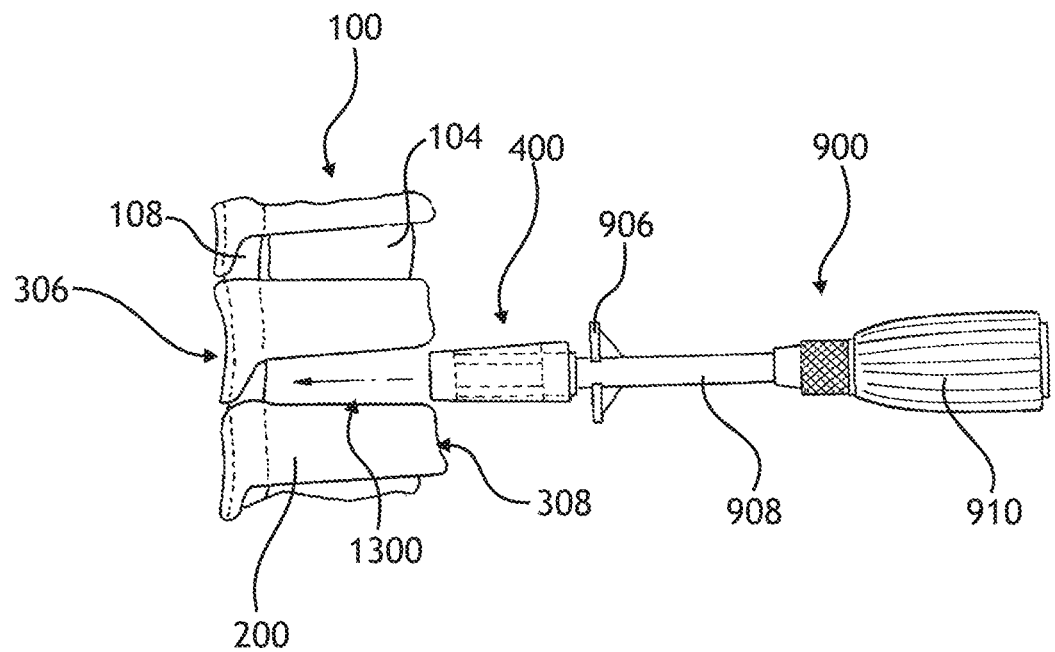
FIG. 13 shows a side view of the combined intervertebral stabilization implant and intervertebral stabilizer insertion tool shown in FIG. 10, immediately prior to insertion of the intervertebral stabilization implant into a vertebral column.
Figure 14:
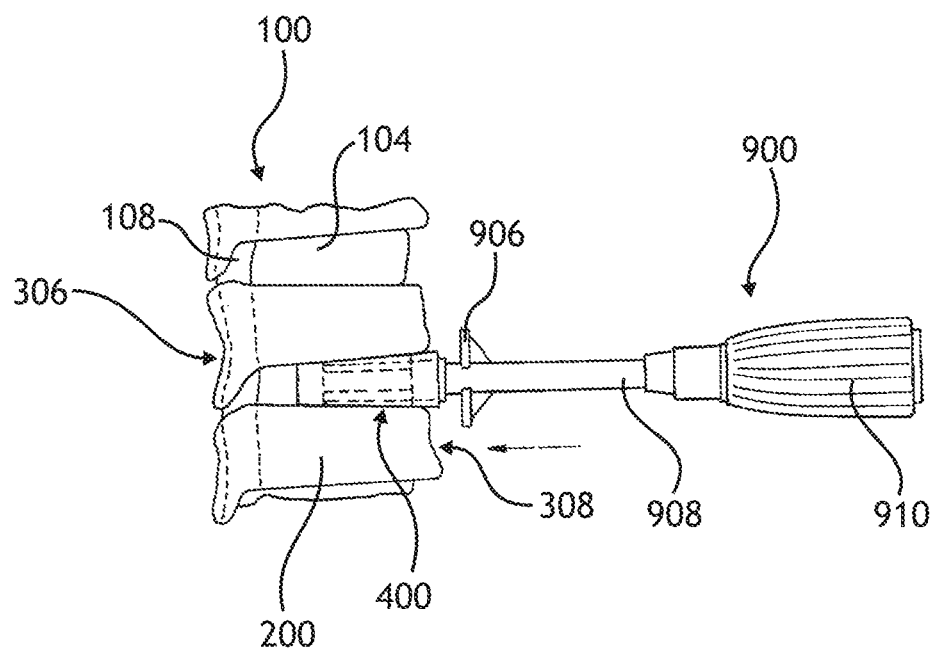
FIG. 14 shows a side view of the combined intervertebral stabilization implant and intervertebral stabilizer insertion tool shown in FIG. 10, partway through insertion of the intervertebral stabilization implant into a vertebral column.

Referring to FIG. 13 and FIG. 14, a surgeon may manipulate a combined intervertebral stabilization implant 400 and intervertebral stabilizer insertion tool 900 according to the present invention to approach the disc space 1300 previously occupied by an unhealthy cartilaginous intervertebral disc 104 from the anterior regions 308 of the vertebral bodies 200 adjacent to the disc space 1300. Depth control posts 906 on the insertion tool 900 may form an axis substantially parallel to an axis defined by a vertebral column 100 containing the vertebrae 102 adjacent to the disc space 1300. The surgeon may then position the implant 400 to interpose between the cortical rims 206 of the vertebral bodies 200 adjacent to the space 1300.

Figure 15:
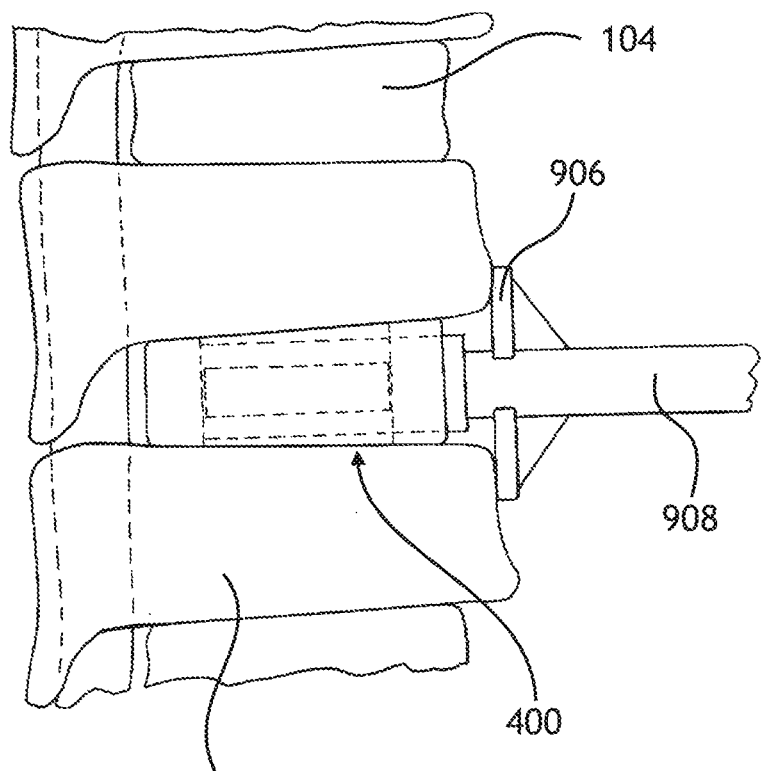
FIG. 15 shows a side view of the combined intervertebral stabilization implant and intervertebral stabilizer insertion tool shown in FIG. 10, after insertion of the intervertebral stabilization implant into a vertebral column, but before the intervertebral stabilizer insertion tool is removed.
Figure 16:
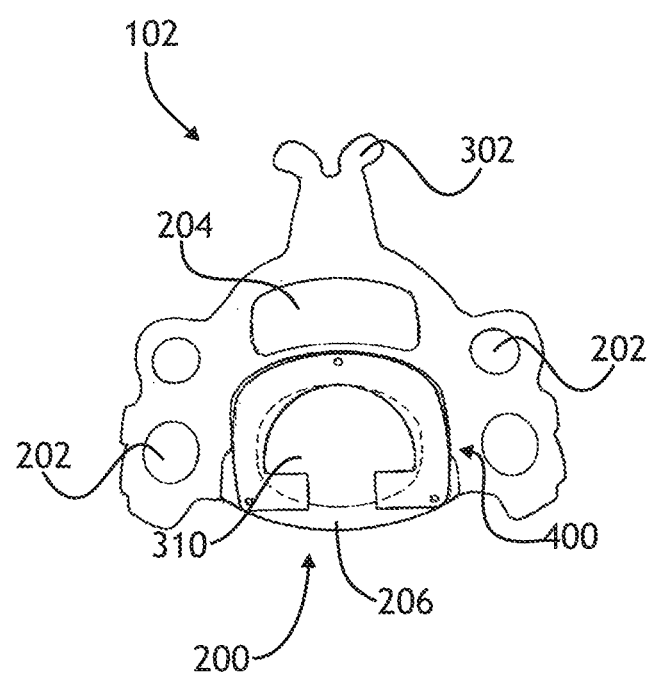
FIG. 16 shows a top view of a vertebra after an embodiment of an intervertebral stabilization implant according to the present invention has been inserted.

Referring to FIG. 15 and FIG. 16, optimal placement of a vertebral spacer is between the cortical rims 206 of adjacent vertebral bodies 200, at the posterior regions 306 of the vertebral bodies 200. Such placement is difficult to achieve because the posterior region 306 of the vertebral body 200 is directly adjacent to the spinal canal 204 which contains the spinal cord 108. A surgeon inserting a vertebral spacer cannot see the posterior region 306 of the vertebral body 200 during insertion; therefore, a surgeon may risk damaging the spinal cord 108 by inserting the spacer too far. A combined intervertebral stabilization implant 400 and intervertebral stabilizer insertion tool 900 with one or more depth control posts 906 according to the present invention may allow a surgeon to safely place the implant 400 between the cortical rims 206 of adjacent vertebral bodies 200 at the posterior regions 306 of the vertebral bodies 200. A depth control post 906 disposed on the shaft 908 of the insertion tool 900 may make contact with one or more of the vertebrae 102 adjacent to the disc space 1300 where the surgeon is inserting the implant 400. The depth control post 906 may allow the combined intervertebral stabilization implant 400 and intervertebral stabilizer insertion tool 900 to travel a predetermined distance into the space 1300 such that when the depth control post 906 makes contact with the vertebrae 102, at least part of the intervertebral spacer 412 of the implant 400 interposes between the cortical rims 206 of the adjacent vertebral bodies 200 at the posterior regions 306 of the vertebral bodies 200.

Figure 17:
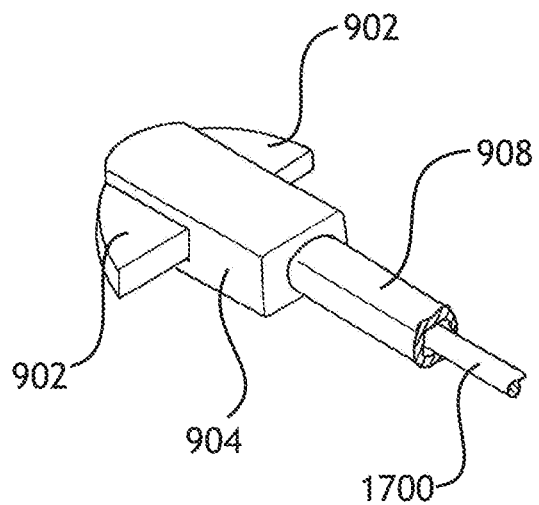
FIG. 17 shows a perspective sectional view of an embodiment of an intervertebral stabilizer insertion tool according to the present invention, with retractable positioning arms fully extended.
Figure 18:
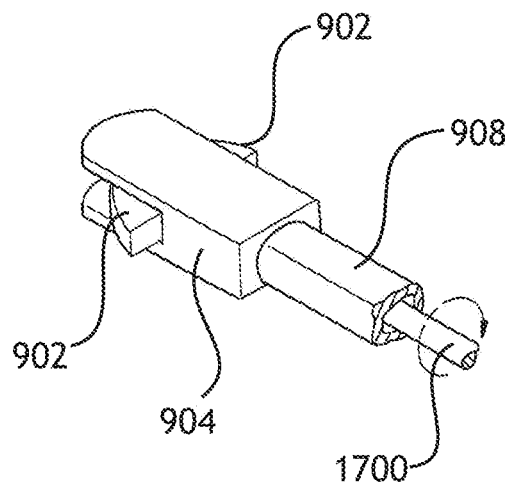
FIG. 18 shows a perspective sectional view of the embodiment of the intervertebral stabilizer insertion tool shown in FIG. 17, with retractable positioning arms partially retracted.
Figure 19:
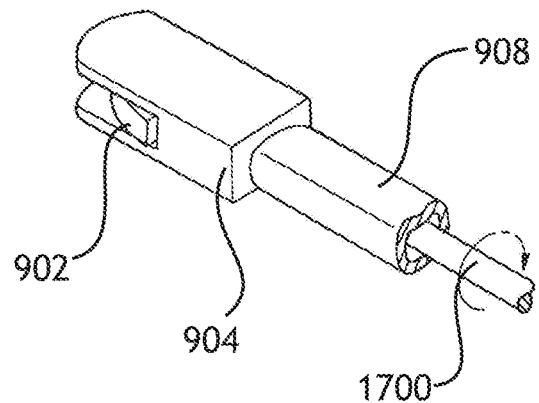
FIG. 19 shows a perspective sectional view of the embodiment of the intervertebral stabilizer insertion tool shown in FIG. 17, with retractable positioning arms fully retracted.

Once the surgeon has positioned the intervertebral stabilization implant 400, the surgeon may remove the intervertebral stabilizer insertion tool 900. Referring to FIG. 17, FIG. 18 and FIG. 19, in one embodiment of an intervertebral stabilizer insertion tool 900 according to the present invention, the surgeon may retract retractable positioning arms 902 into an interlockable positioning head 904 of the intervertebral stabilizer insertion tool 900. The surgeon may actuate a retractable positioning arm actuator 1700, functionally connecting one or more retractable positioning arms 902 to a retractable positioning arm retracting knob 914 through an elongated shaft 908. The surgeon may turn the retractable positioning arm retracting knob 914 and thereby retract the retractable positioning arms 902 into the interlockable positioning head 904. The surgeon may then withdraw the insertion tool 900, leaving the implant 400 in place.

Figure 20:
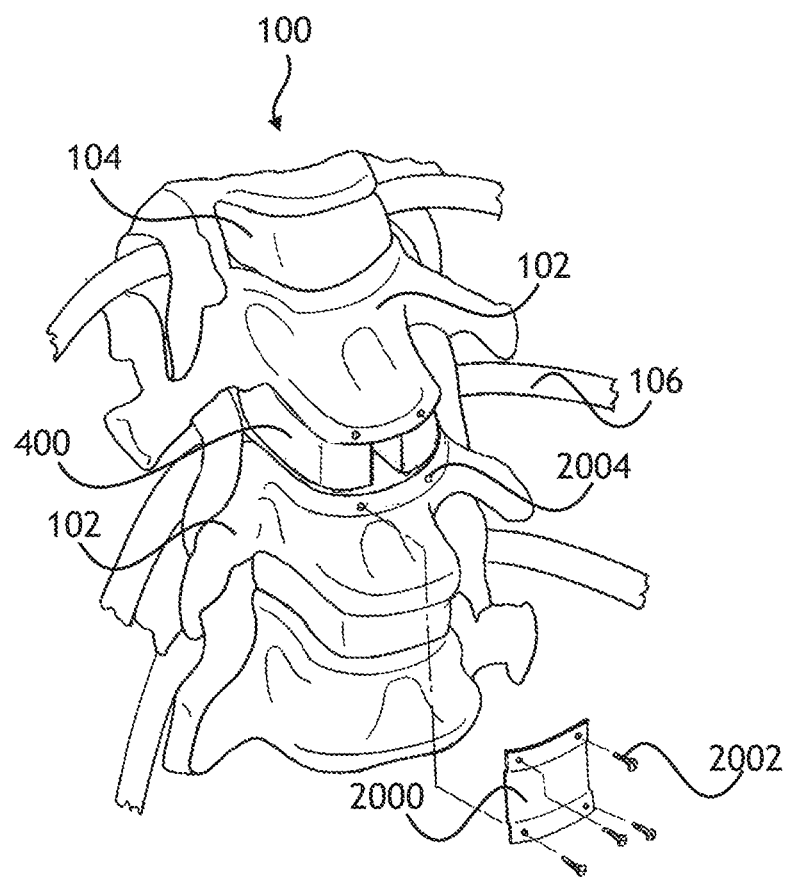
FIG. 20 shows a perspective view of a vertebral column after an embodiment of an intervertebral stabilization implant according to the present invention has been inserted, but before an anterior vertebrae implant plate has been attached to vertebrae in the spinal column adjacent to the intervertebral stabilization implant.

Referring to FIG. 20, once a surgeon has inserted an intervertebral stabilization implant 400 into a vertebral column 100, the surgeon may attach an anterior vertebrae implant plate 2000 to the vertebrae 102 adjacent to the intervertebral stabilization implant 400. The surgeon drills a plurality of screw holes 2004 into the anterior regions 308 of the vertebral bodies 200, corresponding to pre-drilled screw holes in the implant plate 2000. The surgeon then attaches the implant plate 2000 to the vertebrae 102 with implant plate screws 2002. The implant plate 2000 further stabilizes the vertebral column 100. The implant plate 2000 and implant plate screws 2002 may be made from any material suitable for stabilizing two or more vertebrae 102 which is safe for implantation in a vertebral column 100, such as titanium.

Figure 21:
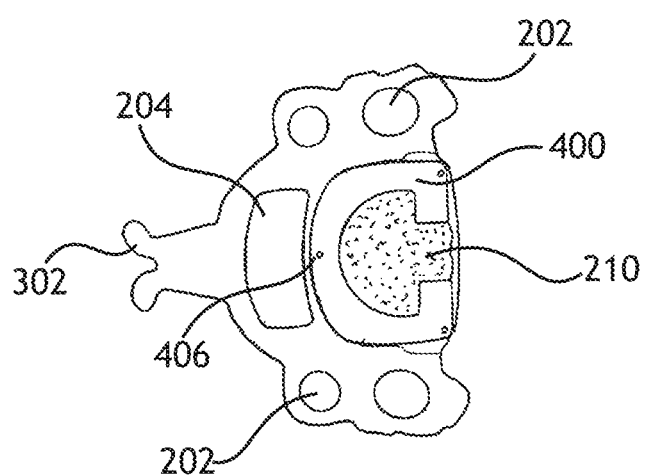
FIG. 21 shows a top view of a vertebra after an embodiment of an intervertebral stabilization implant according to the present invention has been inserted, and after bone-growth inducing material has been inserted into an interlockable cavity of the intervertebral stabilization implant.

Referring to FIG. 21, after inserting an intervertebral stabilization implant 400 according to the present invention, and withdrawing the intervertebral stabilizer insertion tool 900, a surgeon may pack bone-growth inducing material 210 into an interlockable cavity 402 of the implant 400. Because the interlockable cavity 402 is not completely circumscribed by the intervertebral spacer 412, a surgeon may position the implant 400 in a vertebral column 100 before packing bone-growth inducing material 210 into the interlockable cavity 402. Packing bone-growth inducing material 210 into the interlockable cavity 401 after the implant 400 has been inserted reduces the likelihood of gaps 312 between the bone-growth inducing material 210 and the vertebrae 102 adjacent to the implant 400. Where such gaps 312 form, successful fusion is unlikely; therefore, by using an intervertebral stabilization implant 400 according to the present invention, a surgeon increases a patient's probability of successful fusion.

Figure 22:
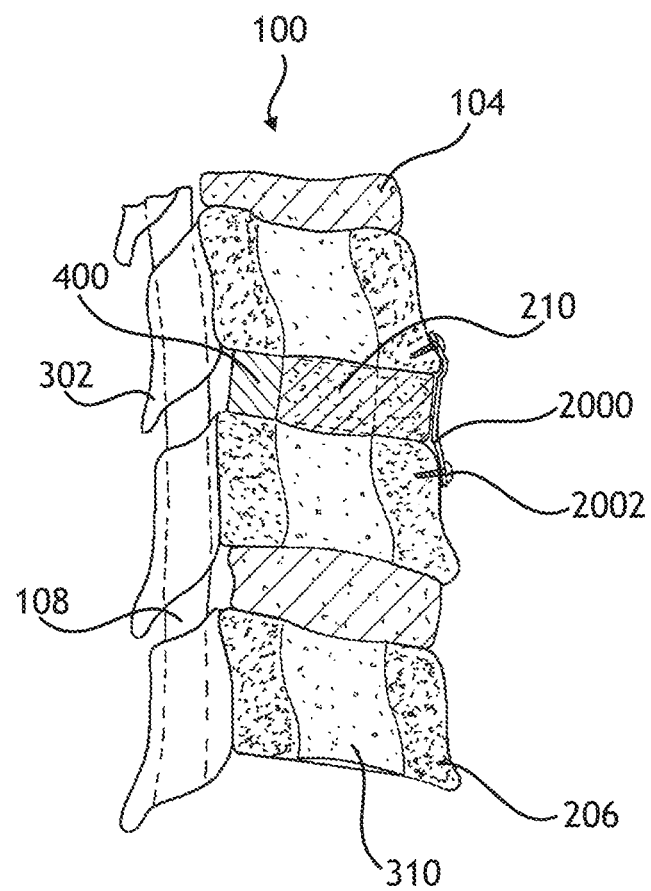
FIG. 22 shows a side, sectional view of a vertebral column after an embodiment of an intervertebral stabilization implant according to the present invention has been completely implanted, including insertion of the intervertebral stabilization implant, insertion of bone-growth inducing material, and installation of an anterior vertebrae implant plate.

Referring to FIG. 22, when the surgery is complete an intervertebral stabilization implant 400 interposes between the cortical rims 206 of two adjacent vertebral bodies 200 in a vertebral column 100. Bone-growth inducing material 210 may fill an interlockable cavity 402 of the implant 400, leaving no gaps between the bone-growth inducing material 210 and the adjacent vertebral bodies 200. A surgeon attaches an anterior vertebrae implant plate 2000 to the anterior s 308 of the adjacent vertebral bodies 102 with implant plate screws 2002 to provide additional stabilization of the vertebral column 100. Because the intervertebral stabilization implant 400 interposes between the denser cortical rims 206 of the vertebral bodies 200 rather than the cancellous bone 310 at the center of the vertebral bodies 200, post surgical subsidence is no longer an issue.

Figure 23:
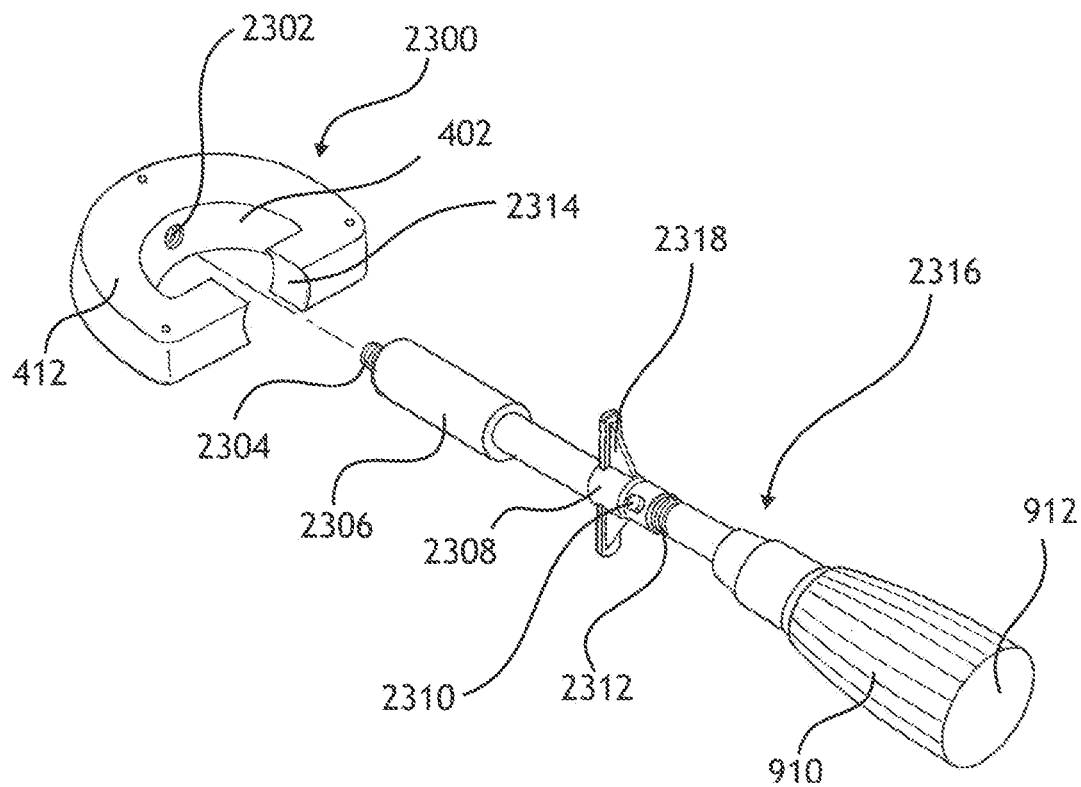
FIG. 23 shows a perspective view of another embodiment of an intervertebral stabilizer insertion tool according to the present invention.

Referring to FIG. 23, another embodiment of an intervertebral stabilization implant 2300 according to the present invention may have an intervertebral spacer 412 for interposing between the cortical rims 206 of adjacent vertebral bodies 200 in place of an unhealthy cartilaginous intervertebral disc 104. The implant 2300 may have an interlockable cavity 402 defined by the intervertebral spacer 412, with a threaded insertion tool receiver 2302 in the posterior surface of the interlockable cavity 402. The threaded insertion tool receiver 2302 engages a threaded implant connector 2304 disposed on the distal of an elongated shaft 908 of another embodiment of an intervertebral stabilizer insertion tool 2316 according to the present invention. The intervertebral stabilization implant 2300 may have one or more contoured position control arms 2314 disposed on the intervertebral spacer 412 to transfer a rotational force to the implant 2300 for the purpose of controlling the orientation and position of the implant 400 between two adjacent vertebrae 102 in the vertebral column 100. A surgeon may apply such force to an intervertebral stabilizer insertion tool 2300 about an axis substantially parallel to an axis defined by a vertebral column 100, An embodiment of an intervertebral stabilizer insertion tool 2316 according to the present invention may have a handle 910 with a strike surface 912 disposed on the proximal end of the handle 910, and an elongated shaft 908 extending from the distal end of the handle 910. The intervertebral stabilizer insertion tool may have a contoured positioning arm 2306 disposed on the distal end of the shaft 908. The contoured positioning arm 2306 may push against one or more contoured position control arms 2314 on an intervertebral stabilization implant 2300 to transfer a rotational for to the implant 2300 when such force is applied to the insertion tool 2316 about an axis substantially parallel to an axis defined by a vertebral column 100. The insertion tool 2316 may have a threaded implant connector 2304 disposed on the distal end of the shaft 908 or the distal end of a contoured positioning arm 2306 to engage a threaded insertion tool receiver 2302 defined by the contact surface of an interlockable cavity 402 of an implant 2300. A surgeon inserting the implant 2300 may insert the implant 2300 between the cortical rims 206 of two adjacent vertebral bodies 200, then rotate the insertion tool 2316 by rotating the handle 910 about an axis defined by the shaft 908 to disengage the threaded implant connector 2304 of the insertion tool 2316 from the threaded insertion tool receiver 2302 of the implant 2300, and then withdraw the insertion tool 2316 leaving the implant 2300 in place.

The intervertebral stabilizer insertion tool 2316 may have one or more adjustable depth control stops 2308 disposed on the shaft 908. In one embodiment of an adjustable depth control stop 2308, the depth control stop 2308 may have depth control protrusions 2318 disposed on the depth control stop 2308, extending along an axis substantially perpendicular to an axis defined by the shaft 908 of the insertion tool 2316. The adjustable depth control stop 2308 slides along the shaft 908 of the insertion tool 2316, such that the depth control protrusions 2318 may be positioned some distance from the distal end of the shaft 908, at the discretion of a surgeon. The surgeon may the insert an intervertebral stabilization implant 2300 connected to the insertion tool 2316 into a space defined by two adjacent vertebrae 102 in a vertebral column 100, and the depth control protrusions 2318 may make contact with the anterior regions 308 of the vertebral bodies 200 of those vertebrae 102 when the intervertebral spacer 412 of the implant 2300 interposes between the cortical rims 206 of the vertebral bodies 200. The adjustable depth control stop 2308 may have a depth control lock 2310 to secure the adjustable depth control stop 2308 at a desired distance from the distal end of the shaft 908. The depth control lock 2310 may be a screw traveling on an axis perpendicular to an axis defined by the shaft 908 such that the screw creates additional friction between the shaft 908 and the adjustable depth control stop 2308.

Another embodiment of the adjustable depth control stop 2308 may include a depth control slide 2312 disposed on the surface of the shaft 908. The depth control slide 2312 may be a threaded section of the surface of the shaft 908 to engage a complimentary threaded section of the adjustable depth control stop 2308 so that the adjustable depth control stop 2308 may be moved closer to or further from the distal end of the shaft 908, according to the judgment of a surgeon, by rotating the adjustable depth control stop 2308 about an axis defined by the shaft 908. The adjustable depth control stop 2308 may have a depth control lock 2310 to prevent the adjustable depth control stop 2308 from moving once a surgeon determines an appropriate setting for the adjustable depth control stop 2308.

Figure 24:
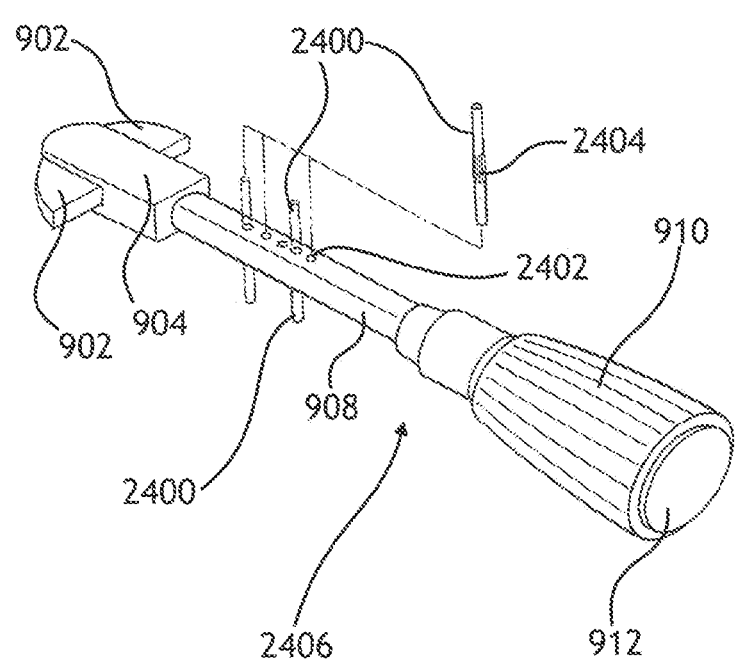
FIG. 24 shows a perspective view of another embodiment of an intervertebral stabilizer insertion tool according to the present invention.

Referring to FIG. 24, another embodiment of an adjustable depth control stop according to the present invention may comprise a plurality of regularly spaced depth control pin holes 2402 defined by an elongated shaft 908 of an intervertebral stabilizer insertion tool 2406, such that a depth control pin 2400 inserted into one of the depth control pin holes 2402 may protrude from the shaft 908, substantially perpendicular to an axis defined by the shaft 908. The depth control pin holes 2402 receive depth control pins 2400 placed by a surgeon, based on the surgeon's judgment and empirical measurements. The surgeon may then insert an intervertebral stabilization implant 400, interlocked with the insertion tool 2406, into a vertebral column 100 so that an intervertebral spacer 412 of the implant 400 may interpose between the cortical rims 206 of two adjacent vertebral bodies 200 when at least one depth control pin 2400 contacts the anterior 308 of at least one vertebral body 200. The adjustable depth control stop may comprise a depth control pin retainer 2404. The depth control pin retainer 2404 may be disposed on each depth control pin 2400 to prevent the depth control pin 2400 from spontaneously moving once placed by a surgeon in a depth control pin hole 2402. The depth control pin retainer 2404 may be a region of a depth control pin 2400 designed to induce friction between the depth control pin 2400 and the depth control pin hole 2402.

A surgeon utilizing the present invention may insert an intervertebral stabilization implant 400 between the dense cortical rims 206 of adjacent vertebral bodies 200 in a vertebral column 100. The invention includes an implant 400 with an interlockable cavity 402 for positioning the implant 400, and an insertion tool 900 with an interlockable positioning head 904 for positioning the implant 400 and one or more depth control stops to prevent the surgeon inserting the implant 400 too far. The interlockable cavity 402 also allows the surgeon to pack bone-growth inducing material 210 into the implant 400 after the implant 400 is inserted.

It is believed that the present invention and many of its attendant advantages will be understood by the foregoing description, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. An intervertebral stabilizer implantation kit comprising:

An intervertebral stabilization implant comprising:
an intervertebral spacer for transferring a load from a cortical rim of a first vertebra to the cortical rim of a second vertebra, having a semi-circular shape configured to generally conform to a shape and size of a cortical rim, and with a varying cross-sectional thickness substantially conforming to the a clinically determined optimal distance between said first vertebra and said second vertebra;
an interlockable cavity for receiving bone-growth inducing material, said interlockable cavity having a semi-circular shape with a substantially constant radius, configured to provide a contact surface for positioning the intervertebral stabilization implant by receiving and distributing a load from an implant insertion tool to move the intervertebral spacer toward a posterior portion of a vertebral column, defined by said intervertebral spacer, wherein said interlockable cavity is open on three sides;
two position control arms defining an open side of the interlockable cavity, each position control arm comprising a curved contact surface for contacting a cylindrical implant insertion tool, each curved contact surface defining an axis substantially perpendicular to an axis defined by the load from the cortical rim of the first vertebra to the cortical rim of the second vertebra, the position control arms further defining a flat contact surface defining the interlockable cavity for receiving a load from an implant insertion tool to move the intervertebral spacer toward an anterior portion of a vertebral column; and
a threaded insertion tool receiver defined by said intervertebral spacer, disposed in an interior surface of the intervertebral spacer opposite the open side of said interlockable cavity defined by the position control arms and defining an axis orthogonal to a plane defined by interior surfaces of the position control arms,
an intervertebral stabilizer insertion tool comprising:
a handle having a mallet striking surface;
an elongated shaft extending from said handle;
an adjustable vertebra contacting depth control stop for defining a maximum insertion depth into a disc space between two vertebrae, comprising:
a depth control slide surrounding said elongated shaft for adjusting a position of said depth control stop;
at least one depth control post disposed on said depth control slide for contacting a vertebra; and
a depth control lock functionally connected to said depth control slide for securing said depth control slide at a clinically determined optimal position along said elongated shaft;
an interlockable positioning head having one or more retractable positioning arms for precisely controlling a positioning of an intervertebral stabilization implant, disposed on an end of said elongated shaft, interlocked with said interlockable cavity in said intervertebral stabilization implant; and
a retractable positioning arm actuator for retracting said one or more retractable positioning arms, operably connected to said one or more retractable positioning arms.

2. The kit of claim 1, wherein said depth control slide defines a threaded portion configured to engage a threaded portion defined by said elongated shaft.

* * * * *